(12) United States Patent
Engell et al.

(10) Patent No.: US 9,567,372 B2
(45) Date of Patent: Feb. 14, 2017

(54) USE OF ANILINE IN THE RADIOSTABILIZATION OF OXIME LIGATION

(75) Inventors: Torgrim Engell, Oslo (NO); Nigel Osborn, Amersham (GB)

(73) Assignee: GE Healthcare Limited (GB)

( * ) Notice: Subject to any disclaimer, the term of this patent is extended or adjusted under 35 U.S.C. 154(b) by 0 days.

(21) Appl. No.: 13/996,020

(22) PCT Filed: Dec. 15, 2011

(86) PCT No.: PCT/US2011/065036
§ 371 (c)(1),
(2), (4) Date: Jun. 20, 2013

(87) PCT Pub. No.: WO2012/087725
PCT Pub. Date: Jun. 28, 2012

(65) Prior Publication Data
US 2013/0274436 A1 Oct. 17, 2013

Related U.S. Application Data

(60) Provisional application No. 61/425,399, filed on Dec. 21, 2010.

(51) Int. Cl.
| | |
|---|---|
| *A61K 38/12* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 7/64* | (2006.01) |
| *A61K 47/48* | (2006.01) |
| *A61K 51/04* | (2006.01) |

(52) U.S. Cl.
CPC ............... *C07K 7/64* (2013.01); *A61K 47/48* (2013.01); *A61K 51/0497* (2013.01)

(58) Field of Classification Search
CPC .......... A61K 38/00; C07K 16/00; C07K 17/06
See application file for complete search history.

(56) References Cited

U.S. PATENT DOCUMENTS

| | | |
|---|---|---|
| 4,451,451 A | 5/1984 | Rimmer |
| 7,914,768 B2 | 3/2011 | Storey et al. |

FOREIGN PATENT DOCUMENTS

| | | |
|---|---|---|
| WO | 2004037297 | 5/2004 |
| WO | 2006/030291 | 3/2006 |
| WO | 2009/016180 | 2/2009 |

OTHER PUBLICATIONS

Glaser et al., Amino Acids, 2009, 37:717-724, published online: Nov. 15, 2008.*
Aniline Catalyzes Imine Formation, Chemical & Engineering News: Latest News-Aniline Catalyzes Imine Formation, available on-line: Nov. 29, 2006. Also appeared in print Dec. 4, 2006, p. 11.*
Reaction rate definition (available online at: http://groups.molbiosci.northwestern.edu/holmgren/Glossary/Definitions/Def-R/reaction_rate.html, last updated on Jul. 26, 2004).*
Walt Volland, Percent Yield Definition and Example, Oct. 12, 2009, available online at http://www.800mainstreet.com/6/0006-007-percent-yield.html.*
Benton, FCC Catalyst Increases Isobutylene Yield at European Refinery—Oil & Gas Journal, May 1, 1995, available on-line at: http://www.ogj.com/articles/print/volume-93/issue-18/in-this-issue/refining/fcc-catalyst-increases-isobutylene-yield-at-european-refinery.html.*
Dirksen et al., Angew. Chem. Int. Ed., 2006, 45, 7581-7584.*
Harki, et.al., Proceedings of the National Academy of Sciences of the United States of American, vol. 105. No. 35, Sep. 2, 2008 pp. 13039-13044.
Flavell, et.al., Jounral of the American Chemical Society, vol. 130, No. 28, Jul. 1, 2008 pp. 9106-9112.
Indrevoll, et.al. Bioorganic & Medicinal Chmeistry Letters., vol. 16. No. 24, Dec. 15, 2006, pp. 6190-6193.
Glaser, et.al., Bioconjugate Chemistry, vol. 19, No. 4, Apr. 2008, pp. 951-957.
Dirksen, et.al. Bioconjugate Chemistry, vol. 19, No. 12, Dec. 17, 2008, pp. 2543-2548.
Dirksen, et.al. Angewandte Chemie. International Edition, vol. 45, No. 45, Nov. 20, 2006, pp. 7581-7584.
Araujo PLB, et.al. Xpress Polymer Letters, 2007, pp. 385-390.
Battle, et.al. The Journal of Nuclear Medicine, vol. 52, No. 3, Mar. 1, 2011, pp. 424-430.
PCT/US2011/065036 ISRWO Dated Apr. 18, 2012.
Morrison et al. "Use of a Novel Arg-Gly-Asp Radioligand, 18F-AH111585, to Determine Changes in Tumor Vascularity After Antitumor Therapy", J Nuclear Medicine, 50(1):116-122 (Jan. 2009).

\* cited by examiner

*Primary Examiner* — Hasan Ahmed
*Assistant Examiner* — Kaipeen Yang
(74) *Attorney, Agent, or Firm* — Wood IP LLC

(57) ABSTRACT

A method of radiostabilizing an oxime ligation or imine formation reaction using aniline is described.

12 Claims, 2 Drawing Sheets

USE OF ANILINE IN THE RADIOSTABILIZATION OF OXIME LIGATION

This application is a filing under 35 U.S.C. 371 of international application number PCT/US2011/065036, filed Dec. 15, 2010, which claims priority to U.S. application No. 61/425,399 filed Dec. 21, 2010, the entire disclosure of which is hereby incorporated by reference.

FIELD OF THE INVENTION

The present invention relates to a method of both radiostabilizing and catalyzing an oxime ligation reaction using aniline.

BACKGROUND OF THE INVENTION

The use of aniline in oxime ligations or imine formation has been shown to be effective in increasing the overall reaction rate and to allow such reactions to occur at less acidic pH values (A. Dirksen, et al., "Nucleophilic Catalysis of Oxime Ligation Angew. Chem. Int. Ed. 2006, 45, 7581-7584 A. Dirksen, T. Hackeng and P. Dawson). However, such reactions have been limited to non-radiolabeled compounds.

As described in more detail below, it has now been surprisingly found that aniline can be used to radiostabilize the oxime ligation or imine formation reaction of radiolabeled reactants with the unexpected results of both improved reaction kinetics and significant radiostabilization.

SUMMARY OF THE INVENTION

The invention provides a radiostabilizing method comprising the step of reacting a radiolabeled aldehyde (I) with an aminooxy (II) in the presence of aniline (III) to form radiolabeled imine-oxy (IV), each as described herein:

Scheme A

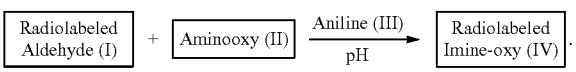

The invention also provides a radiostabilizing method comprising the step of reacting an aldehyde (V) with a radiolabeled aminooxy (VI) in the presence of aniline (III) to form radiolabeled imine-oxy (VII), each as described herein:

Scheme B

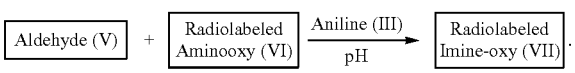

The invention further provides a radiostabilizing method comprising the step of reacting a radiolabeled aldehyde (VIII) with an aminooxy (IX) in the presence of aniline (III) to form radiolabeled imine-oxy (X), each as described herein:

Scheme C

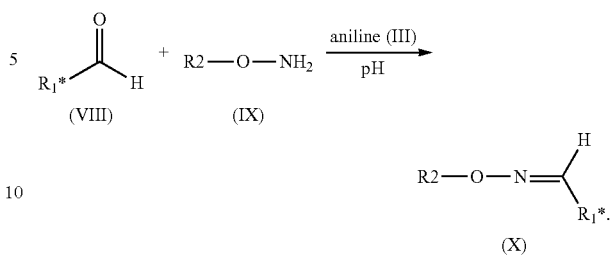

The invention further provides a radiostabilizing method comprising the step of reacting an aldehyde (XI) with a radiolabeled aminooxy (XII) in the presence of aniline (III) to form radiolabeled imine-oxy (XIII), each as described herein:

Scheme D

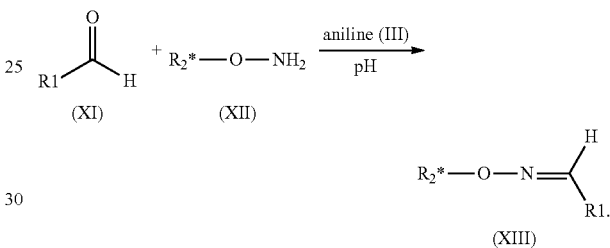

The use of aniline in a radiostabilizing method of the invention provides two distinct advantages: (i) enhanced reaction kinetics and, surprisingly, (ii) significant radiostabilization. Hence aniline as used in a radiostabilizing method of the invention exhibits unexpected dual functionality as both a catalyst and a radiostabilizer. The increase in radiostabilization allows for an increase in yield of the resulting radiolabeled imine-oxy especially at high radioactivity.

DETAILED DESCRIPTION OF THE INVENTION

Radiolabeled Aldehyde

Figure 1:
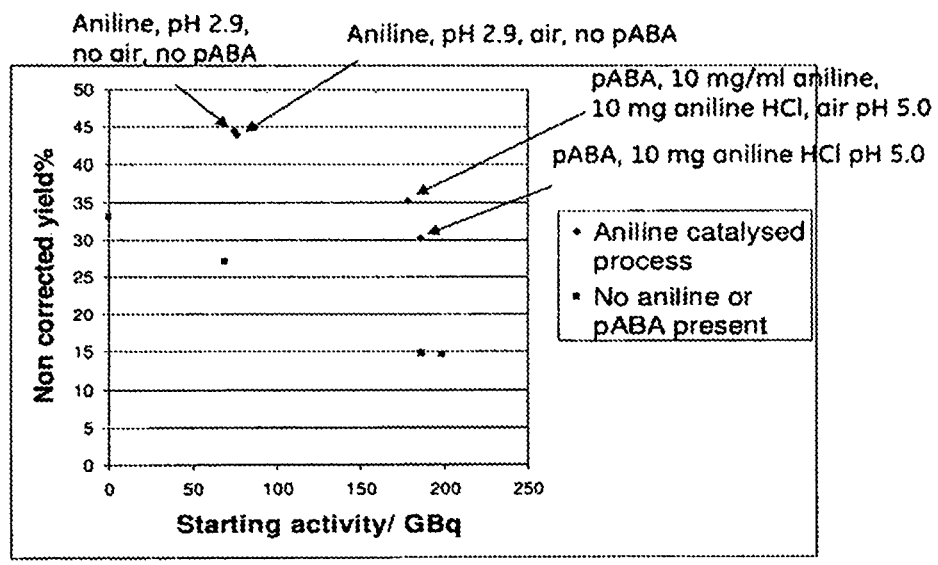
FIG. 1 illustrates the results for the production of crude fluciclatide on FASTlab.

The radiolabeled aldehyde (I) for use in a radiostabilizing method of the present invention can be any aldehyde labeled with at least one radioisotope, as described herein, capable of reacting with an aminooxy as described herein. In one embodiment of the invention, the radiolabeled aldehyde is a compound of formula (VIII):

wherein:

R₁* can be any radiolabeled organic or biological moiety. According to the invention, a radiolabeled organic or biological moiety is an organic or biological moiety containing at least one radioisotope/radionuclide, each as described herein:

The radiolabel of $R_1^*$ can be any radioisotope or radionuclide known in the art including but not limited to those imaging moieties described in US2008/0279771, which is incorporated in its entirety by reference. Preferably the radioisotope or radionuclide is a radioisotope/radionuclide suitable for imaging (e.g., PET, SPECT). In one embodiment, the radionuclide is a radioisotope suitable for PET imaging. Even more preferably, the radionuclide is $^{11}C$, $^{13}N$, $^{15}O$, $^{68}Ga$, $^{62}Cu$, $^{18}F$, $^{76}Br$, $^{124}I$, or $^{125}I$; even more preferably, the radionuclide is $^{18}F$. In one embodiment, the radionuclide is a radioisotope suitable for SPECT imaging. Even more preferably, the radionuclide is $^{99m}Tc$, $^{111}In$, $^{67}Ga$, $^{201}Tl$, $^{123}I$, or $^{133}Xe$; even more preferably, the radionuclide is $^{99m}Tc$ or $^{123}I$.

In one embodiment of the invention, R1* is a radiolabeled organic moiety selected from alkyl, alkenyl, alkynyl, aryl, cycloalkyl, heterocyclyl, heteroaryl, and cycloalkyl. In another embodiment, R1* is a radiolabeled organic moiety selected from $C_1$-$C_{20}$ alkyl, $C_2$-$C_{20}$ alkenyl, $C_2$-$C_{20}$ alkynyl, $C_5$-$C_{20}$ aryl, $C_3$-$C_{20}$ cycloalkyl, $C_5$-$C_{20}$ heterocyclyl, $C_5$-$C_{20}$ heteroaryl, or $C_3$-$C_{20}$ cycloalkyl group.

In one embodiment of the invention, R1* is a radiolabeled biological moiety selected from amino acids, peptides, and vectors.

Examples of suitable radiolabeled aldehyde include, but are not limited to:

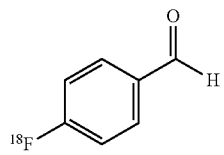

[18F]-parabenzaldehyde; and those described in US20100068139A1 and US2004/080492A1, each of which is incorporated herein by reference. In one embodiment of the invention, the radiolabeled aldehyde is [18F]-parabenzaldehyde.

A radiolabeled aldehyde, as described herein, can be prepared by methods known in the literature and art.

Aminooxy

The aminooxy (II) for use in a radiostabilizing method of the present invention can by any compound containing an amino-oxy moiety (i.e., —O—NH₂) capable of reacting with a radiolabeled aldehyde as described herein. In one embodiment of the invention, the aminoxy (II) is a compound of formula (IX):

$$R2—O—NH_2 \quad (IX)$$

wherein R2 can be any organic or biological moiety. In one embodiment of the invention, R2 is an organic moiety selected from alkyl, alkenyl, alkynyl, aryl, cycloalkyl, heterocyclyl, heteroaryl, and cycloalkyl. In another embodiment, R2 is an organic moiety selected from $C_1$-$C_{20}$alkyl, $C_2$-$C_{20}$alkenyl, $C_2$-$C_{20}$alkynyl, $C_5$-$C_{20}$aryl, $C_3$-$C_{20}$cycloalkyl, $C_5$-$C_{20}$ heterocyclyl, C5-$C_{20}$ heteroaryl, or $C_3$-$C_{20}$cycloalkyl group.

In one embodiment of the invention, R2 is a biological moiety selected from amino acids, peptides, and vectors.

Examples of suitable aminooxy compounds include, but are not limited to:

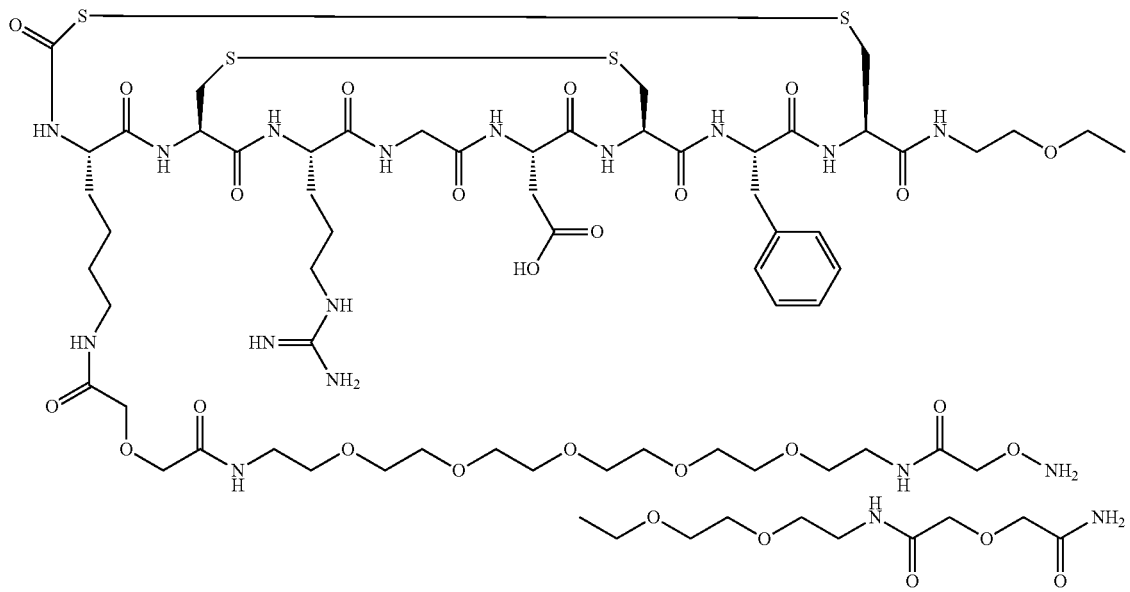

(Fluciclatide peptide precursor)

and cMET:

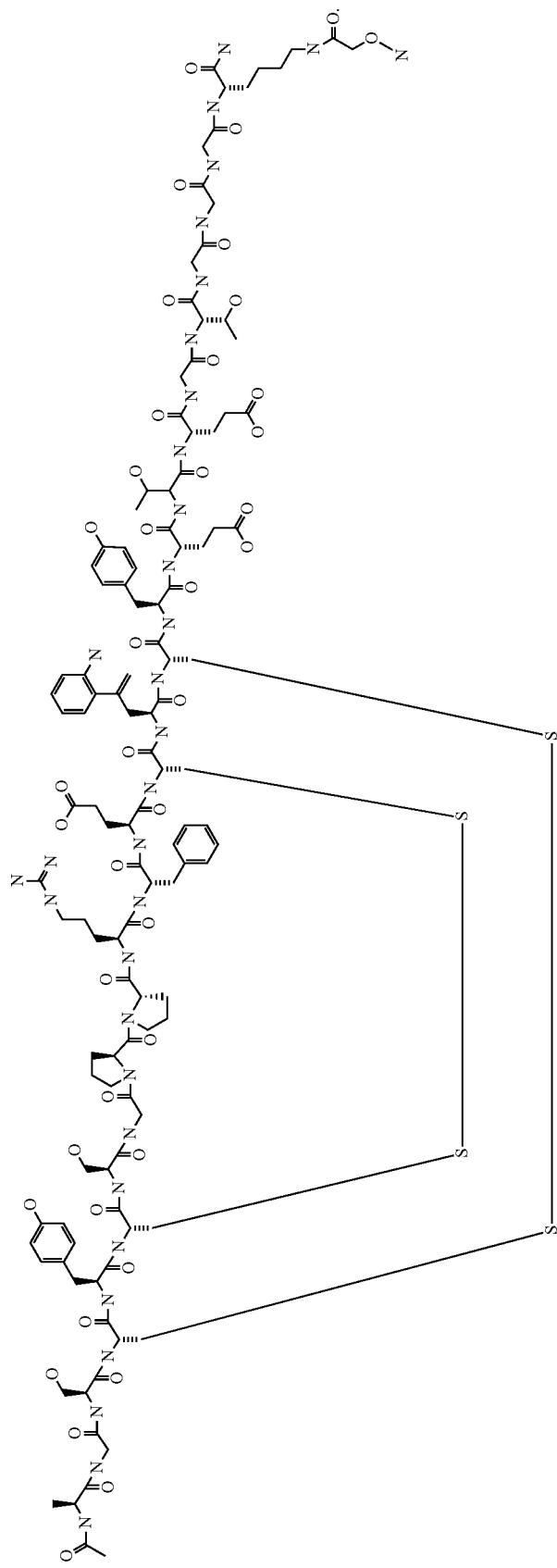

An aminoxy, as described herein, can be prepared by methods known in the literature and art.

Aniline

Aniline (III) for use in a radiostabilizing method of the present invention can be any aniline known in the art (e.g., Adam R. Blanden, et al., *Bioconjugate Chem.*, 2011, 22 (10), pp 1954-1961; Mikkel B. Thygesen, et al., *J. Org. Chem.*, 2010, 75 (5), pp 1752-1755) including commercially available aniline of the following formula:

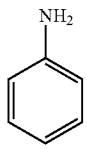

or a salt thereof (e.g., bromide, chloride, iodide, HBr, HCl, HI, trifluoroacetic acid (TFA)) or a derivative thereof (e.g., 4-methoxyaniline, 4-nitroaniline, 2,6-dimethylaniline, deuterated aniline derivatives (i.e., aniline compound in which at least one hydrogen has been replaced with a deuterium), polymer-bound aniline (see e.g. Sigma-Aldrich product number 564761)). An aniline derivative is any aniline based compound that can be used to achieve a radiostabilizing method of the invention. In one embodiment of the invention, aniline (III) for use in a radiostabilizing method of the present invention can also be a mixture of anilines as described herein (e.g. a mixture of aniline and aniline hydrochloride).

In one embodiment of the invention, aniline (III) used in the reaction of the invention is in its commercially available HCl salt form:

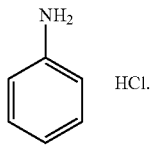

In one embodiment of the invention, aniline (III) can be used alone or in combination with commercially available para-amino benzoic acid (pABA).

In one embodiment of the invention, aniline (III) can be used alone or in combination with other radiostabilizers known in the art. Examples of a suitable radiostabilizer requiring neutral or basic pH conditions include, but are not limited to: p-aminobenzoic acid, gentisic acid (2,5-dihydroxybenzoic acid), tocopherol, hydroquinone, di-t-butylphenol, and di-t-butylatedhydroxytoluene). Radiostabilizers that do not require a deprotonation can also be used. Examples of known radical traps include, but are not limited to, galvinoxyl (2,6-Di-tert-butyl-α-(3,5-di-tert-butyl-4-oxo-2,5-cyclohexadien-1-ylidene)-p-tolyloxy, free radical; commercially available form Sigma-Aldrich), TEMPO (2,2,6,6-Tetramethyl Piperidine-1-oxide), DPPH (diphenylpicrylhydrazyl), 1,2-diphenylethylene, Beta-carotene, and DMPO (5,5-dimethyl-1-pyrroline-1-oxide).

pH

A radiostabilizing method of the present invention can be performed at about pH 1.0-7.0. In one embodiment of the invention, the pH range is about 2.0-5.0. In one embodiment of the invention, the pH range is about 2.8-4.2. In one embodiment of the invention, the pH range is about 2.8-3.5.

Radiolabeled Imine-Oxy (IV)

Radiolabeled imine-oxy (IV) of a radiostabilizing method of the present invention is the oxime ligation reaction product of radiolabeled aldehyde (I) and aminooxy (II) in the presence of aniline (III) and pH, each as described herein.

In one embodiment of the invention, the radiolabeled imine-oxy is a compound of formula (X):

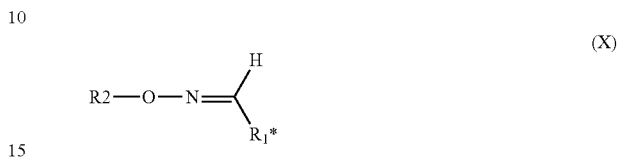

wherein R2 and $R_1^*$ are each as described herein.

Aldehyde

The aldehyde (V) for use in a radiostabilizing method of the present invention can be any aldehyde known in the art capable of reacting with radiolabeled aminooxy, as described herein. In one embodiment of the invention, the aldehyde is a compound of formula (XI):

wherein R1 can be any organic or biological moiety.

In one embodiment of the invention, R1 is an organic moiety selected from alkyl, alkenyl, alkynyl, aryl, cycloalkyl, heterocyclyl, heteroaryl, and cycloalkyl. In another embodiment, R1 is an organic moiety selected from $C_1$-$C_{20}$ alkyl, $C_2$-$C_{20}$ alkenyl, $C_2$-$C_{20}$ alkynyl, $C_5$-$C_{20}$ aryl, $C_3$-$C_{20}$ cycloalkyl, $C_5$-$C_{20}$ heterocyclyl, $C_5$-$C_{20}$ heteroaryl, or $C_3$-$C_{20}$ cycloalkyl group.

In one embodiment of the invention, R1 is a biological moiety selected from amino acids, peptides, and vectors.

Examples of suitable aldehydes include, but are not limited to, benzaldehyde:

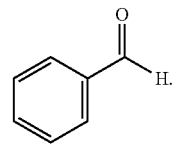

An aldehyde, as described herein, is commercially available or can be prepared by methods known in the literature and art.

Radiolabeled Aminooxy

The radiolabeled aminooxy (VI) for use in a radiostabilizing method of the present invention can by any aminoxy compound as described herein that contains at least one radioisotope as described herein. In one embodiment of the invention, the radiolabeled aminooxy (VI) is a compound of formula (XII):

$$R_2^*-O-NH_2 \quad (XII)$$

wherein $R_2^*$ can be any radiolabeled organic or biological moiety where a radiolabeled organic or biological moiety is an organic or biological moiety containing at least one radioisotope/radionuclide, each as described herein.

The radiolabel of $R_2^*$ can be any radioisotope or radionuclide known in the art including but not limited to those imaging moieties described in US2008/0279771, which is incorporated in its entirety by reference. Preferably the radioisotope or radionuclide is a radioisotope/radionuclide suitable for imaging (e.g., PET, SPECT). In one embodiment, the radionuclide is a radioisotope suitable for PET imaging. Even more preferably, the radionuclide is $^{11}C$, $^{13}N$, $^{15}O$, $^{68}Ga$, $^{62}Cu$, $^{18}F$, $^{76}Br$, $^{124}I$, or $^{125}I$; even more preferably, the radionuclide is $^{18}F$. In one embodiment, the radionuclide is a radioisotope suitable for SPECT imaging. Even more preferably, the radionuclide is $^{99m}Tc$, $^{111}In$, $^{67}Ga$, $^{201}Tl$, $^{123}I$, or $^{133}Xe$; even more preferably, the radionuclide is $^{99m}Tc$ or $^{123}I$.

A radiolabeled aminooxy, as described herein, can be prepared by methods known in the literature and art.

Radiolabeled Imine-Oxy (VII)

Radiolabeled imine-oxy (VII) of a radiostabilizing method of the present invention is the oxime ligation reaction product of aldehyde (V) and radiolabeled aminooxy (VI) in the presence of aniline (III) and pH, each as described herein.

In one embodiment of the invention, the radiolabeled imine-oxy is a compound of formula (XIII):

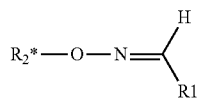

(XIII)

wherein R1 and $R_2^*$ are each as described herein.

In one embodiment, a radiostabilizing method of the present invention is automated by means of an automated radiosynthesis apparatus. There are several commercially-available examples of such apparatus, including TRACERlab™ and FASTlab™ (both commercially available from GE Healthcare a division of General Electric Company). Such apparatus commonly comprises a "cassette", often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges used in post-radiosynthetic clean up steps. Accordingly, the present invention provides a cassette for an automated radiostabilizing method of the present invention.

EXAMPLES

Example 1

Fluciclatide Radiostabilized Conjugation Reaction

4-[18F]fluorobenzaldehyde was reacted with aminoxy, AH111695 (fluciclatide peptide precursor):

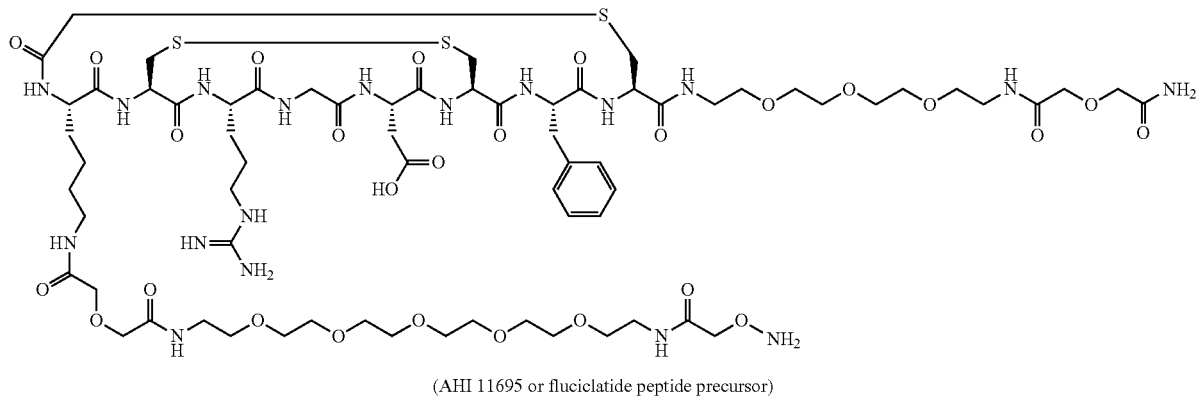 [SMILES: N=C(N)NCCC[C@@H]1NC(=O)[C@@H]2CSSC[C@H](NC(=O)[C@H](CC(=O)O)NC(=O)CNC1=O)C(=O)N[C@@H](Cc1ccccc1)C(=O)N[C@H](C(=O)NCCOCCOCCOCCNC(=O)COCC(N)=O)CSCC(=O)N[C@@H](CCCCNC(=O)COCC(=O)NCCOCCOCCOCCOCCOCCNC(=O)CON)C(=O)N2]

(AHI 11695 or fluciclatide peptide precursor)

in the presence of aniline at various pH ranges to give fluciclatide. The radiochemical results of the reaction is illustrated in FIG. 1.

FIG. 1 illustrates the results for the production of crude fluciclatide on FASTlab.

The diamonds are for the non-radiostabilised conjugation reaction (i.e., without aniline or pABA) and clearly show the linear link between the amount of starting activity and the non corrected yield. The triangles show the results for the production of crude Fluciclatide on FASTlab under radiostabilized conjugation reaction conditions (i.e., addition of pABA at pH 6.1 to the conjugation reaction added around 50% to the non corrected yield and the presence of air helped further stabilise the conjugation. Lowering of pH by around one pH unit added a further 5% to the yield and the addition of further aniline improved the RCP by a similar amount.

FIG. 1 clearly shows the radiostabilisation effect of aniline on the conjugation reaction between fluciclatide peptide precursor and [18F]fluorobenzaldehyde. The rhombus-shaped (non-radiostabilized) points show the clear correlation between the non corrected yield % of the reaction in the absence of any radiostabiliser. However, the triangular points (radiostabilized) clearly show the dramatic impact of using a radiostabiliser.

The presence of 10 mg aniline hydrochloride at pH 5.0 or a mixture of 10 mg aniline and aniline hydrochloride at the same pH sees a dramatic improvement in the non corrected yield %. However, the presence of the radiostabiliser para amino benzoic acid, does not preclude this as being in part responsible for the radiostabilisation of the conjugation reaction. However, removing p-amino benzoic acid altogether in the presence or absence of air results in a dramatic shift in the non corrected yield %, establishing that results are from the presence of aniline itself rather than any impact from the presence of pABA.

Comparative Example 1

Fluciclatide Non-Radiostabilized Conjugation Reaction

Figure 2:
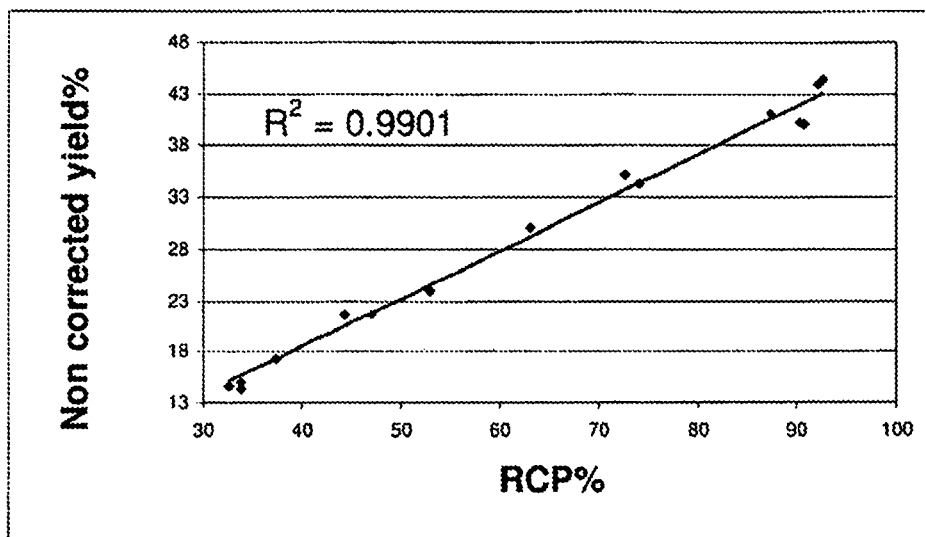
FIG. 2 shows the correlation between yield and RCP % for a non radiostabilised reaction.

FIG. 2 illustrates the strong correlation between the yield and the RCP% for the non radiostabilised reaction between the fluciclatide peptide precursor and [18F]fluorobenzaldehyde. The regressional analysis of the dataset has forced the line through the point of origin. Clearly the yield is directly correlated with the RCP % of fluciclatide, with no other significant factor being required to explain the variation observed.

Example 2

5 mg of fluciclatide peptide precursor is added to 1.7 ml of aniline hydrochloride in water (10 mg/ml) and 1.15 ml of ethanol is added containing the [18F]fluorobenzaldehyde. The reaction is allowed to progress for 5 minutes at 60° C.

What is claimed is:

1. A radiostabilizing method for preparing a radioimaging agent comprising the step of reacting a radiolabeled aldehyde (I) with an aminooxy (II) in the presence of aniline (III) at pH 2.8-3.5 to form imine-oxy (IV):

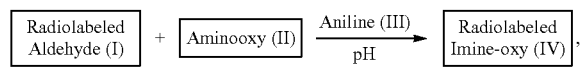

wherein aniline is present in an amount that provides a catalytic effect and a radiostabilizing effect, wherein the amount of aniline includes a radiostabilizing amount of aniline that is additive to the amount of aniline that provides the catalytic effect, and wherein the radiochemical yield % of imine-oxy (IV) is increased above the yield % of said method without said radiostabilizing amount of aniline.

2. The radiostabilizing method of claim 1, wherein said radiolabeled aldehyde (I) is a compound of formula (VIII):

wherein $R_1^*$ is a radiolabeled organic or biological moiety.

3. The radiostabilizing method of claim 2, wherein said radiolabeled organic moiety is alkyl, alkenyl, alkynyl, aryl, cycloalkyl, heterocyclyl, heteroaryl, or cycloalkyl and wherein said radiolabeled biological moiety is an amino acid, peptide, or vector.

4. The radiostabilizing method of claim 1, wherein the radiolabel of $R_1^*$ is a radioisotope suitable for PET or SPECT imaging.

5. The radiostabilizing method of claim 1, wherein said radiolabeled aldehyde is [18F]parabenzaldehyde.

6. The radiostabilizing method of claim 1 wherein said aminooxy (II) is a compound of formula (IX):

$$R_2—O—NH_2 \qquad (IX)$$

wherein R2 can be any organic or biological moiety.

7. The radiostabilizing method of claim 6, wherein said aminooxy (II) is

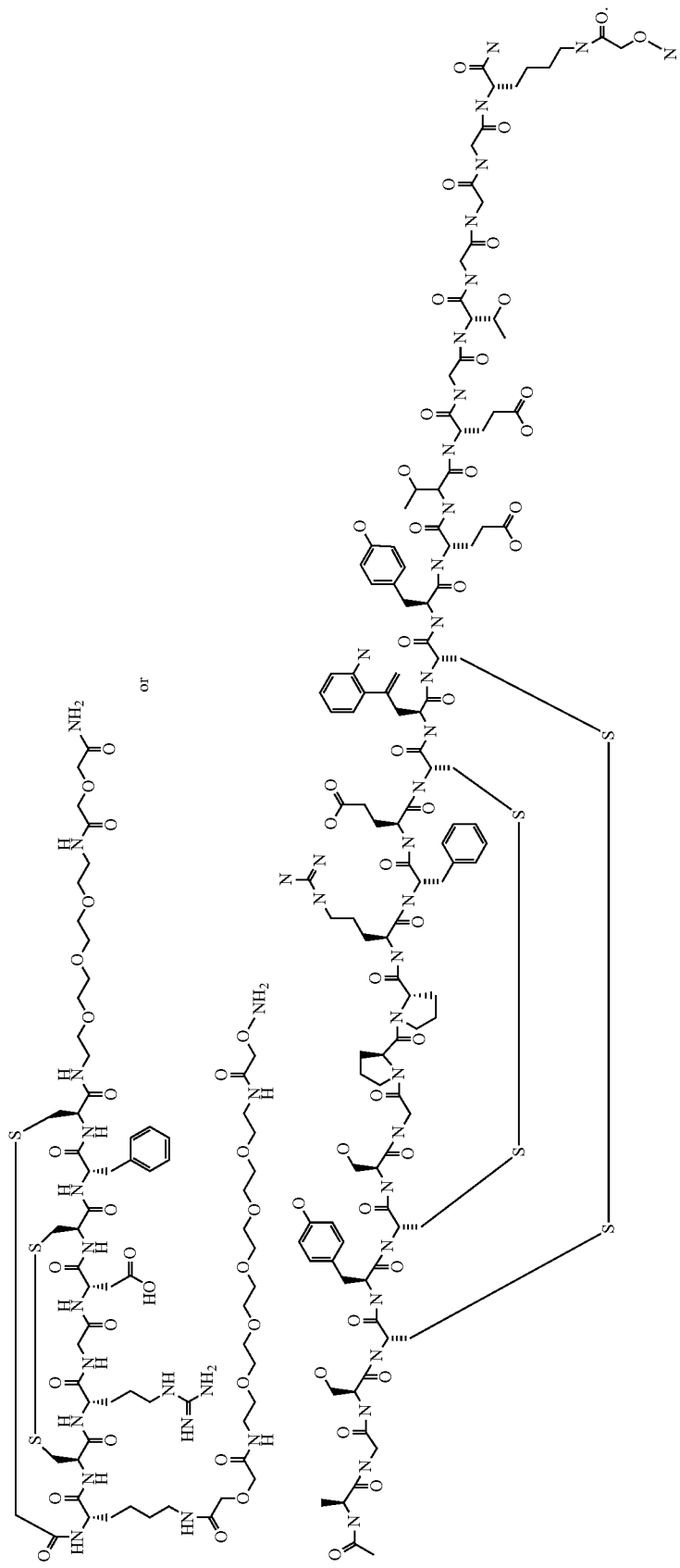

8. The radiostabilizing method of claim 6, wherein said radiolabeled imine-oxy is a compound of formula (X):

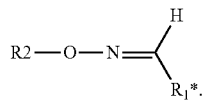
(X)

9. A radiostabilizing method comprising the step of reacting a radiolabeled aldehyde (VIII) with an aminooxy (IX) in the presence of aniline (III) at pH 2.8-3.5 to form imine-oxy (X):

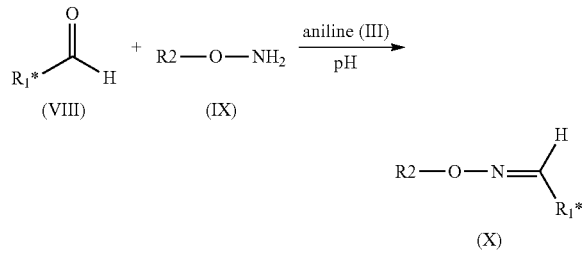

wherein:
 R$_1$* is organic or biological moiety labeled with at least one radioisotope or radionuclide;
 R$_2$ is an organic or biological moiety; and
 aniline is present in an amount that provides a catalyzing effect and a radiostabilizing effect, wherein the amount of aniline includes a radiostabilizing amount of aniline that is additive to the amount of aniline that provides the catalytic effect, and wherein the radiochemical yield % of imine-oxy (X) is increased above the yield % of said method without said radiostabilizing amount of aniline.

10. The radiostabilizing method of claim 1, wherein said aniline is of the following formula:

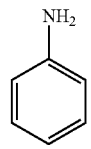

a salt or derivative thereof or a mixture thereof.

11. The radiostabilizing method of claim 10, wherein said aniline is:

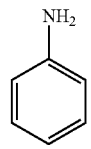 HCl.

12. The radiostabilizing method of claim 10, wherein said aniline is used in combination with para-amino benzoic acid or with a radiostabilizer.

* * * * *